United States Patent [19]

Katsumata et al.

[11] Patent Number: 4,489,160
[45] Date of Patent: Dec. 18, 1984

[54] PLASMID PCG2

[75] Inventors: Ryoichi Katsumata, Machida; Tetsuo Oka, Yokohama; Akira Furuya, Kawasaki, all of Japan

[73] Assignee: Kyowa Hakko Kogyo Co., Ltd., Tokyo, Japan

[21] Appl. No.: 410,887

[22] Filed: Aug. 24, 1982

[30] Foreign Application Priority Data

Aug. 26, 1981 [JP] Japan ................................. 56/133557

[51] Int. Cl.³ ...................... C12N 1/20; C12N 15/00; C12N 1/00
[52] U.S. Cl. .................................. 435/253; 435/172.3; 435/317; 935/29; 935/72; 935/60
[58] Field of Search ........................ 435/317, 172, 253

[56] References Cited

U.S. PATENT DOCUMENTS 4,332,900 6/1982 Manis et al. .......................... 435/317
4,362,817 12/1982 Reusser ................................ 435/317

FOREIGN PATENT DOCUMENTS 2076853 12/1981 United Kingdom .

Primary Examiner—Alvin E. Tanenholtz
Attorney, Agent, or Firm—Fitzpatrick, Cella, Harper & Scinto

[57] ABSTRACT

Disclosed is a novel vector, plasmid pCG2, and a process of producing plasmid pCG2 from *Corynebacterium glutamicum*.

6 Claims, 1 Drawing Figure

PLASMID PCG2

BACKGROUND OF THE INVENTION

The present invention relates to a novel isolated plasmid, plasmid pCG2, and a process for producing the same.

The role of vectors in gene engineering is stated clearly in *Recombinant Molecules: Impact on Science and Society*, Miles International Symposium Series No. 10, edited by R. F. Beers and E. G. Basset, Raven Press, New York. The usefulness of plasmids as vectors in gene engineering is recognized on the host-vector system of *Escherichia coli*. Recombinant DNA technology has also been developed on industrially useful microorganisms other than *Escherichia coli*, such as amylase-producing *Bacillus Subtilis*, antibiotic-producing Actinomycetes and alcohol-producing yeasts. Since vectors are essential for recombinant DNA technology, plasmids and phages have been searched for in these microorganisms.

Microorganisms belonging to *Corynebacterium glutamicum* or analogous species thereof are used in industrial production of useful substances such as glutamic acid, lysine and the like. A plasmid, or phage, useful as a vector in the microorganims belonging to the genus Corynebacterium is essential to establish recombinant DNA technology on these microorganisms.

Summary of the Invention

In accordance with the present invention, plasmid pCG2 is produced from Corynebacterium glutamicum 225–218. The process for producing plasmid pCG2 comprises culturing *Corynebacterium glutamicum* 225–218 in a nutrient medium, disrupting the cultured cells, and recovering plasmid pCG2 from the disrupted cells. Plasmid pCG2 thus produced has been found to be useful as a vector to establish recombinant DNA technology on microorganisms belonging to the genus Corynebacterium.

Plasmid pCG2 is characterized by a molecular weight of about 6.6 kilobases and the following cleavage sites for restriction endonucleases:

| Restriction enzyme | Number of cleavage sites |
| --- | --- |
| HindIII | 3 |
| KpnI | 2 |
| BamHI | 1 |
| PstI | 1 |
| HpaI | 1 |
| EcoRI | 0 |
| SalI | 0 |
| BglII | 0 |

Microorganisms belonging to *Corynebacterium glutamicum*, especially the strain *Corynebacterium glutamicum* 225–218 ATCC 31832, carries plasmid pCG2. In another embodiment of the invention, plasmid pCG2 isolated from *Corynebacterium glutamicum* 225–218 is introduced into a microorganism other than 225–218 belonging to the genus Corynebacterium.

Detailed Description of the Invention

Figure 1:
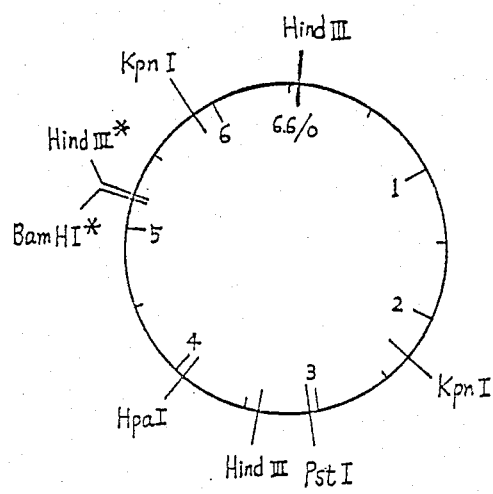

Plasmid pCG2 has a molecular weight of about 6.6 kilobases and the cleavage site mentioned below for several conventional restriction endonucleases. The properties show that plasmid pCG2 is useful as a cloning vector in microorganisms belonging to *Corynebacterium glutamicum* and related microorganisms and as a reagent for the study of recombinant DNA technology because a desired gene can be inserted in the plasmid and the inserted plasmid is autonomously replicated in the microorganisms.

Plasmid pCG2 is produced from the novel 225–218 strain which has been recently isolated from soil. Taxonomic studies of the 225–218 strain were carried out according to the description in *Manual of Microbiological Methods* by the Society of American Bacteriologist Committee on Bacteriological Technique (1957).

The properties of the 225–218 strain are set forth below:

I. Morphological characteristics of cells of the 225–218 strain:

Usually ellipsoidal or short rods 0.7–1.0 by 1.0–3.0μ; Pleomorphic due to snapping division and branching cells; Gram positive; Non-motile; Non-spore-forming.

II. Culture characteristics on a nutrient medium:

On an agar plate, a single, circular, lustrous and pale yellow colony; on a slant, a similar pale yellow opaque colony; on an agar stab, abundant growth on surface and weak growth in deep; in a liquid medium, slight growth and slightly flocculent sediment.

III. Physiological characteristics:

| | |
| --- | --- |
| (1) Temperature: | optimum temperature 25–37° C.; growth occurs slightly at 42° C. |
| (2) pH: | optimum pH 7–8; growth occurs at pH 6–9 |
| (3) Thermal resistance: | none |
| (4) Relation to free oxygen: | aerobic |
| (5) Gelatin liquefaction: | none |
| (6) Assimilation of casein: | negative |
| (7) Indole production: | none |
| (8) Catalase: | positive |
| (9) Assimilation of starch: | negative |
| (10) Acid production from glucose, fructose, mannose and maltose; non-acid production from xylose, galactose, lactose and glycerol | |
| (11) Requirement for biotin: positive | |
| (12) Glutamic acid is accumulated in a large quantity in a medium wherein the amount of biotin is restricted. | |
| (13) Lactic acid and α-ketoglutaric acid are accumulated in a medium containing biotin in a high concentration. | |

These characteristics were compared with those of bacteria disclosed in J. Gen. Appl. Microbiol, 73, 279–301 (1967). Since the characteristics coincide well with those of *Corynebacterium glutamicum*, the 225–218 strain is identified as *Corynebacterium glutamicum*. This novel strain has been deposited with the Fermentation Research Institute, Agency of Industrial Science and Techniology, Japan, under accession number FERM-P 5954 and with the American Type Culture Collection, Rockville, Md, USA, under accession number ATCC 31832.

In order to produce plasmid pCG2 from the cells of *Corynebacterium glutamicum* 225–218, the cultured cells have to be disrupted. Since cells of microorganisms belonging to the genus Corynebacterium or related microorganisms when cultivated in a conventional medium are insensitive to a bacteriolytic enzyme such as egg white lysozyme, it is necessary to render them sensitive to such lysozyme prior to use.

To render *Corynebacterium glutamicum* 225–218 sensitive to lysozyme, a method is employed which is used for *Brevibacterium lactofermentum* [Japanese Published Unexamined patent application No. 28896/79] which is analogous to *Corynebacterium glutamicum;* or for *Streptococcus faecalis* [Can. J. Microbiol., 7, 363–373 (1961)] which is gram-positive and insensitive to egg white lysozyme like *Corynebacterium glutamicum.* According to this method, during the log phase cultivation period, penicillin in an amount which does not inhibit or sub-inhibits the growth, usually 0.1–10 U/ml culture liquor, is added to the medium and cultivation is continued for several generations. Lysozyme-sensitive cells are thus obtained.

For culturing, a liquid medium and cultivation methods which are usually used for culturing microorganisms belonging to *Corynebacterium glutamicum* and related microorganisms are employed. The cell walls of cultured cells of Corynebacterium glutamicum 225-218 which are treated with penicillin as mentioned above are easily disrupted with lysozyme. Plasmid pCG2 thus can be condensed and isolated from the disrupted cells by a conventional method such as disclosed in Biochim. Biophys. Acta, 383, 457–463 (1975).

The plasmid pCG2 thus obtained is a deoxyribonucleic acid with a molecular weight of about 6.6 kilobases. Plasmid pCG2 has the following cleavage sites for the following restriction endonucleases:

| Enzyme | Number of cleavage sites |
|---|---|
| Hind III | 3 |
| Kpn I | 2 |
| Bam HI | 1 |
| Pst I | 1 |
| Hpa I | 1 |
| Sal I | 0 |
| Eco RI | 0 |
| Bgl II | 0 |

These enzymes are obtained and named from the following microorganisms:

| | |
|---|---|
| Hind III: | *Haemophilus influenzae* |
| Kpn I: | *Klebsiella pneumoniae* |
| Bam HI: | *Bacillus amyloliquefacience* |
| Pst I: | *Providencia stuartii* |
| Hpa I: | *Haemophilus parainfluenzae* |
| Sal I: | *Streptomyces albus* |
| Eco RI: | *Escherichia coli* |
| Bgl II: | *Bacillus globigii* |

KpnI and HpaI are products of Bethesda Research Laboratories and the other are products of Takara Shuzo Co., Ltd.

The number of cleavage sites for restriction endonucleases is determined by completely digesting plasmid pCG2 in the presence of an excess amount of restriction endonucleases, subjecting the digest to 0.8% agarose gel electrophoresis, and thereafter counting the number of isolated fragments. The molecular weight is determined by measuring the molecular weight of each fragment in the digested plasmid pCG2 based on the standard curve plotted with electrophoretic distances on agarose gel electrophoresis for the fragments obtained by digesting λphage DNA of *Escherichia coli* with HindIII [J. Mol. Biol., 98, 551–564 (1975)] and in the case of plural fragments, summing up the molecular weights.

The cleavage map of plasmid pCG2 for the restriction endonucleases mentioned above are constructed by digesting completely plasmid pCG2 with plural restriction endonucleases and analyzing the resulting DNA fragments by agarose gel electrophoresis.

The thus obtained restriction map of plasmid pCG2 for restriction endonucleases is illustrated in FIG. 1.

Plasmid pCG2 is useful because it is autonomously replicated in industrially important microorganisms belonging to *Corynebacterium glutamicum* and related microorganisms which are used for the production of useful substances such as amino acids, nucleic acids, and the like. Plasmid pCG2, therefore, can be used as a cloning vector in these host microorganisms. Accordingly, it is possible to clone a gene involved in the biosynthesis of useful substances such as amino acid, nucleic acids, and the like or its regulation from the microorganisms belonging to *Corynebacterium glutamicum* and related microorganisms or others in the microorganisms belonging to the genus Corynebacterium or related microorganisms by conventional in vitro recombinant DNA technology. Moreover, the present invention provides a process which increases the productivity of the useful substances by the stimulation of a biosynthetic system based on the amplification of the cloned genetic information.

Since the function of pCG2 to replicate autonomously in the microorganisms belonging to the genus Corynebacterium or related microorganisms is encoded on a part of pCG2 DNA, derivatives of plasmid pCG2, for example, a plasmid wherein a region of plasmid pCG2 is deleted and/or another DNA fragment is inserted in plasmid pCG2, may replicate autonomously. Therefore, it is clear that the DNA obtained by the modification of plasmid pCG2 is useful as well as plasmid pCG2 itself.

As an illustration of the present invention, an example is set forth below.

EXAMPLE 1

(1) Isolation of plasmid pCG2 from the cultured cells of Corynebacterium glutamicum 225-218:

*Corynebacterium glutamicum* 225-218 is cultured with shaking at 30° C. for 18 hours in an NB medium consisting of 20 g of powdered bouillon, 5 g of yeast extract and 1 l of water and adjusted to pH 7.2. Then, 5 ml of the culture is inoculated into 400 ml of a semisynthetic medium consisting of 20 g of glucose, 10 g of $(NH_4)_2SO_4$, 3 g of urea, 1 g of yeast extract, 1 g of $KH_2PO_4$, 0.4 g of $MgCl_2.6H_2O$, 10 mg of $FeSO_4.7H_2O$, 0.2 mg of $MnSO_4.(4-6)H_2O$, 0.9 mg of $ZnSO_4.7H_2O$, 0.4 mg of $CuSO_4.5H_2O$, 0.09 mg of $Na_2B_4O_7.10H_2O$, 0.04 mg of $(NH_4)_6Mo_7O_{24}.4H_2O$, 30 μg of biotin, 1 mg of thiamine hydrochloride and 1 l of water (the pH is adjusted to 7.2). Culturing is carried out with shaking at 30° C. Optical density (OD) at 660 nm is measured with a Tokyo Koden colorimeter and, at the OD value of 0.2, penicillin G is added to the broth to a final concentration of 0.5 U/ml. Cultivation is continued at 30° C.. to an OD value of about 0.6.

Cells are recovered from the culture broth, washed with TES buffer solution (pH 8.0) consisting of (i) 0.03M tri(hydroxymethyl)aminomethane (Tris), (II), 0.005M EDTA and (iii) 0.05M NaCl and thereafter suspended in a lysozyme solution (pH 8.0) consisting of 25% sucrose, 0.1M NaCl, 0.05M Tris and 0.8 mg/ml lysozyme to make 20 ml of a suspension. The suspension is allowed to react at 37° C. for 4 hours. Then, 2.4 ml of 5M NaCl, 0.6 ml of 0.5M EDTA (pH 8.5) and 4.4 ml of a solution of 4% sodium lauryl sulfate and 0.7M NaCl are added successively to the reaction suspension. The mixture is stirred slowly and kept on an ice water bath for 15 hours.

Whole lysate is put into a centrifugation tube and centrifuged under 69,400×g at 4° C. for 60 minutes to obtain a supernatant solution. Polyethyleneglycol 6000 is added to a final concentration of 10% (W/V) to the supernatant. The mixture is stirred slowly to dissolve polyethyleneglycol, 6,000 completely and placed on an ice water bath. After 16 hours, the mixture is subjected to centrifugation under 1,500×g for 10 minutes to obtain a pellet. The pellet is redissolved in 5 ml of TES buffer solution and 2.0 ml of 1.5 mg/ml ethidium bromide is added. Cesium chloride is added to the mixture to adjust the density to 1.580. The solution is centrifuged under 105,000×g at 18° C. for 48 hours.

After the density gradient centrifugation, a circular DNA closed with a covalent bond is found as a high density band located in the lower part of the centrifugation tube by ultraviolet irradiation. The band is taken out from the side of the tube with an injector to obtain a fraction containing plasmid pCG2. The fraction is treated five times with an equal amount of cesium chloride saturated isopropylalcohol solution consisting of 90% by volume of isopropylalcohol and 10% TES buffer solution to remove ethidium bromide. Then, the residue is subjected to dialysis against TES buffer solution.

Two ml of ethanol is added to 1 ml of the dialysate to precipitate pCG2 DNA. The precipitate is recovered by centrifugation and dried in vacuo at −20° C. to obtain 40 μg of plasmid pCG2.

(2) Cleavage specificity with various restriction endonucleases and molecular weight of plasmid pCG2:

In this step, 0.5 μg of plasmid pCG2 prepared above is dissolved in 10 μl of TES buffer solution (pH 8.0) and two folds or more excess restriction endonucleases such as EcoRI, HindIII, BamHI, PstI, SalI, BglII, KpnI and HpaI are added under the suitable conditions for each restriction endonucleases. The digested specimen is applied to horizontal 0.8% agarose gel containing 0.6 μg/ml ethidium bromide and electrophoresis is carried out at a constant additional voltage of 7 V per 1 cm in width for 3-4 hours. The number of fragments formed is counted under ultraviolet irradiation on the gel plate. The molecular weight of each fragment is determined from the electrophoretic distance and that of plasmid pCG2 is determined by summing up. The molecular weight of plasmid pCG2 is determined by reference to a standard curve plotted against electrophoretic distance of DNA fragments of known molecular weights which are produced by the digestion of λ phage DNA and Hind III and subjected to electrophoresis on the same agarose gel as that for plasmid pCG2. The results are illustrated in the following Table 1.

TABLE 1

| Enzyme | Number of cleavage sites | Molecular weight of each fragment (kilobase) | Molecular weight of pCG2 by summing up (kilobase) |
|---|---|---|---|
| Hind III | 3 | 3.45, 1.74, 1.39 | 6.58 |
| Kpn I | 2 | 3.55, 3.10 | 6.65 |
| Bam HI | 1 | 6.58 | 6.58 |
| Pst I | 1 | 6.60 | 6.60 |
| Hpa I | 1 | 6.62 | 6.62 |
| Eco RI | 0 | — | — |
| Sal I | 0 | — | — |
| Bgl II | 0 | — | — |

Analysis of digested fragments of plasmid pCG2 by double digestion is carried out by digesting the plasmid with a restriction endonuclease, concentrating the resulting digested DNA fragments by ethanol precipitation, digesting the concentrated DNA fragments with another restriction endonuclease and subjecting the double-digested fragments to agarose gel electrophoresis. A restriction map of plasmid pCG2 for restriction endonucleases determined from the sizes of digested fragments is illustrated in FIG. 1. Since the cleavage sites for Hind III and Bam HI which are marked with stars are very close to each other, these sites may be reversed.

What is claimed is:

1. An isolated plasmid pCG2 characterized by a molecular weight of about 6.6 kilobases and the following cleavage sites for restriction endonucleases:

| Restriction enzyme | Number of cleavage sites |
|---|---|
| HindIII | 3 |
| KpnI | 2 |
| BamHI | 1 |
| PstI | 1 |
| HpaI | 1 |
| EcoRI | 0 |
| SalI | 0 |
| BglII | 0 |

2. A process for producing plasmid pCG2 which comprises culturing *Corynebacterium glutamicum* 225-218 in a nutrient medium, disrupting the cultured cells and recovering plasmid pCG2 from the disrupted cells.

3. A biologically pure culture of a microorganism belonging to the species *Corynebacterium glutamicum* and carrying plasmid pCG2.

4. A biologically pure culture of a microorganism according to claim 3, which is *Corynebacterium glutamicum* 225-218, ATCC 31832.

5. A biologically pure culture of a microorganism belonging to *Corynebacterium glutamicum* which carries plasmid pCG2 isolated from *Corynebacterium glutamicum* 225-218.

6. A recombinant plasmid constructed from the plasmid pCG2 defined in claim 1 by deleting a DNA region from said plasmid that does not affect its function to replicate autonomously or adding a foreign DNA fragment to said plasmid.

* * * * *

UNITED STATES PATENT AND TRADEMARK OFFICE
CERTIFICATE OF CORRECTION

PATENT NO. : 4,489,160  Page 1 of 2

DATED : December 18, 1984

INVENTOR(S) : RYOICHI KATSUMATA, et al.

It is certified that error appears in the above-identified patent and that said Letters Patent is hereby corrected as shown below:

Cover Page, at Section [56] under "FOREIGN PATENT DOCUMENTS",
   add --0082485  6/1983 European Pat. Off.--

Cover Page, at Section [56] following "FOREIGN PATENT DOCUMENTS"
   insert the following:

--OTHER PUBLICATIONS

D.C. Gross, et al., Chem. Abstr., 92: 142903v (1980)

D.C. Gross, et al., "Indigenous Plasmids from Phyto-
      pathogenic Corynebacterium Species"; J. Gen.
      Microbiol., 115(2), pp. 479-89 (1979)

H. Kaneko, et al., Chem. Abstr., 91: 89549k (1979)

H. Kaneko, et al., Agric. Biol. Chem., Vol. 43,
      No. 4, pp. 867-868 (1979).--

UNITED STATES PATENT AND TRADEMARK OFFICE
CERTIFICATE OF CORRECTION

PATENT NO. : 4,489,160
DATED : December 18, 1984
INVENTOR(S) : RYOICHI KATSUMATA, et al.

It is certified that error appears in the above-identified patent and that said Letters Patent is hereby corrected as shown below:

Column 6, line 60, "or" should read --in Corynebacterium and--.

Column 6, line 62, the following claim should be added:

--7. A recombinant plasmid capable of autonomous replication in Corynebacterium constructed from the plasmid pCG2 defined in Claim 1 by adding a foreign DNA fragment to said plasmid.--

On the title page "6 Claims" should read -- 7 Claims --.

Signed and Sealed this

Eighteenth Day of June 1985

[SEAL]

Attest:

DONALD J. QUIGG

Attesting Officer    Acting Commissioner of Patents and Trademarks